United States Patent
Kabeshita et al.

(10) Patent No.: US 9,268,523 B2
(45) Date of Patent: Feb. 23, 2016

(54) FITTING GOLF BALLS USING ACOUSTIC RESPONSE

(71) Applicant: NIKE, Inc., Beaverton, OR (US)

(72) Inventors: Yutaka Kabeshita, Portland, OR (US);
Nicholas A. Leech, Beaverton, OR (US);
Arthur Molinari, Portland, OR (US);
Nicholas Yontz, Portland, OR (US)

(73) Assignee: Nike Inc., Beaverton, OR (US)

( * ) Notice: Subject to any disclaimer, the term of this patent is extended or adjusted under 35 U.S.C. 154(b) by 228 days.

(21) Appl. No.: 14/153,475

(22) Filed: Jan. 13, 2014

(65) Prior Publication Data

US 2015/0199170 A1 Jul. 16, 2015

(51) Int. Cl.
*G06F 17/00* (2006.01)
*G06F 3/16* (2006.01)
*A63B 37/00* (2006.01)
*G01N 3/30* (2006.01)

(52) U.S. Cl.
CPC ............ *G06F 3/165* (2013.01); *A63B 37/007* (2013.01); *G01N 3/30* (2013.01)

(58) Field of Classification Search
CPC .............. A63B 69/36; A63B 37/0003; A63B 2069/3602
See application file for complete search history.

(56) References Cited

U.S. PATENT DOCUMENTS

| | | | |
|---|---|---|---|
| 4,375,887 A | 3/1983 | Lynch et al. | |
| 6,086,487 A | 7/2000 | Morgan et al. | |
| 6,192,323 B1 | 2/2001 | Boehm | |
| 7,908,907 B1 * | 3/2011 | Nelson | A63B 37/0003 73/65.03 |
| 2009/0017945 A1 * | 1/2009 | Tayama | A63B 24/0021 473/409 |
| 2009/0325721 A1 * | 12/2009 | Esayian | A63B 47/00 473/131 |
| 2011/0009215 A1 | 1/2011 | Ichikawa et al. | |
| 2013/0260914 A1 | 10/2013 | Ishii et al. | |

* cited by examiner

*Primary Examiner* — Joseph Saunders, Jr.
(74) *Attorney, Agent, or Firm* — Quinn Law Group, PLLC

(57) ABSTRACT

An electronic method for matching a user with a golf ball includes playing a first digital audio file to a user via a computer and playing a second digital audio file to the user via the computer. Each of the first digital audio file and the second digital audio file correspond to an acoustic response of a respective golf ball to a standardized impact force. The method then includes receiving an input from the user via the computer, where the input corresponds to a preferred acoustic response selected from the acoustic response of the first golf ball and the acoustic response of the second golf ball. Once the preferred response is determined, the method includes displaying a golf ball model that corresponds to the preferred acoustic response.

15 Claims, 4 Drawing Sheets

FITTING GOLF BALLS USING ACOUSTIC RESPONSE

TECHNICAL FIELD

The present invention relates generally to a method of fitting a consumer with a golf ball using an acoustic response of the ball.

BACKGROUND

Golf balls are manufactured using a variety of processes and materials. The response of the ball when struck by a club may vary as a function of the hardness of the materials chosen. For example, a harder ball will typically travel further when struck by a driver than a softer ball. Likewise, a softer ball will typically spin more when struck by a wedge than a harder ball. Using these generalizations, many golfers will select a ball according to their preference for distance or spin control. These attributes are often referenced on golf ball packaging and advertising.

In addition to distance and spin control, however, many golfers also want a ball that has an expected "feel." Feel is generally a subjective assessment of the response of the ball when struck by a club, though it is largely influenced by the sound of the impact. While the acoustic response of the ball may be an important factor in ball selection to some golfers, it is typically not considered or referenced in current retail practices.

SUMMARY

An electronic method for matching a user with a golf ball includes playing a first digital audio file to a user via a computer and playing a second digital audio file to the user via the computer. Each of the first digital audio file and the second digital audio file correspond to an acoustic response of a respective golf ball to a standardized impact force.

The method then includes receiving an input from the user via the computer, where the input corresponds to a preferred acoustic response selected from the acoustic response of the first golf ball and the acoustic response of the second golf ball. Once the preferred response is determined, the method includes displaying a golf ball model that corresponds to the preferred acoustic response.

Each of the plurality of digital audio files may be stored on a computer and indexed according to the magnitude of an acoustic property selected from a loudness, a peak frequency, and a spectral centroid. Each of the respective first digital audio file and the second digital audio file may be selected from the plurality of digital audio files in an iterative manner according to a user preference for the acoustic property.

The method may further include receiving a preference input from the user corresponding to at least one of a distance preference, a spin tendency, and an audible sensitivity of the user. The preference input may be used to filter the plurality of digital audio files to consider only balls having characteristics that are optimally suited for the user's ability level. Each of the first digital audio file and the second digital audio file may then be selected from this filtered collection of digital audio files.

The standardized impact force may be an impact force generated by dropping the respective golf ball from a predetermined height onto a solid material. Alternatively, the standardized impact force may be an impact force imparted to the respective golf ball by a golf club head swung at a controlled speed and angle.

The above features and advantages and other features and advantages of the present invention are readily apparent from the following detailed description of the best modes for carrying out the invention when taken in connection with the accompanying drawings.

DETAILED DESCRIPTION

Figure 1:
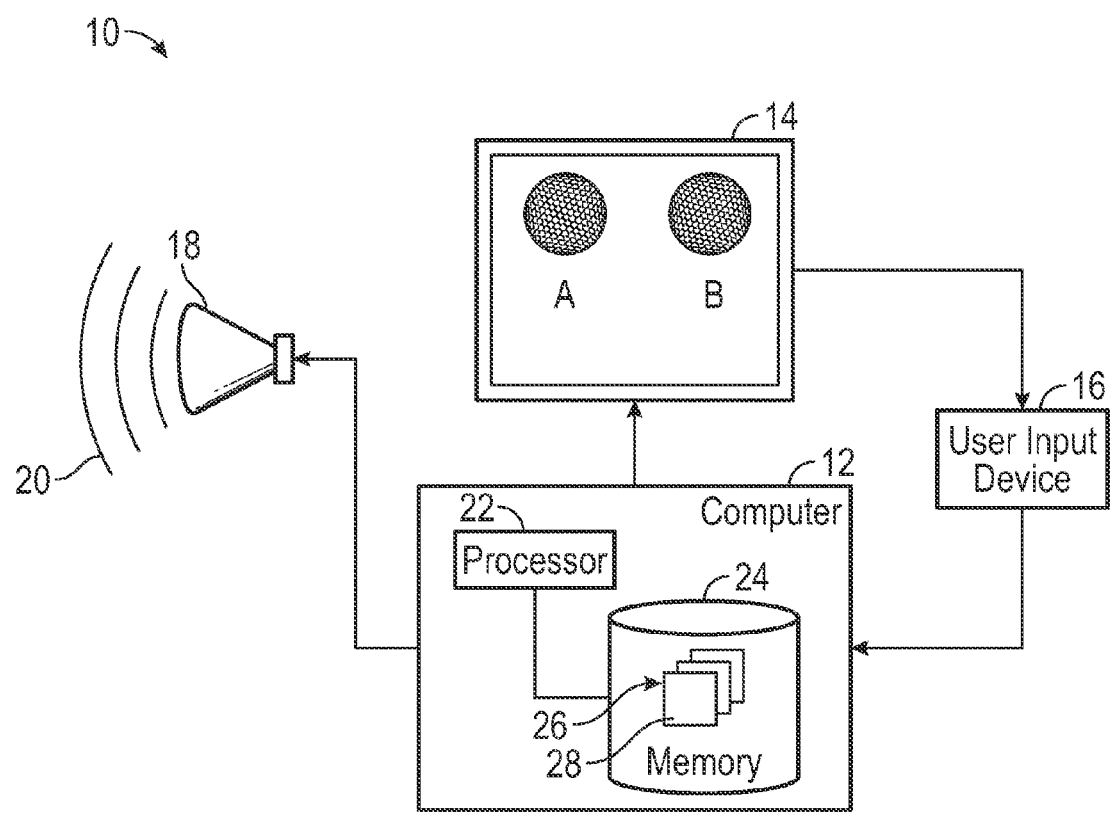
FIG. 1 is a schematic diagram of a system that may be used to match a user with an optimal golf ball model according to that user's preferences.

Referring to the drawings, wherein like reference numerals are used to identify like or identical components in the various views, FIG. 1 schematically illustrates a system 10 that may be used to match a user with an optimal golf ball model according to that user's preferences. In particular, the system 10 is configured to demonstrate the acoustic response of a plurality of golf balls to a standardized impact force in an effort to determine a user's preferred impact sound or ball "feel" (where "feel" is a subjective characteristic of the ball that is highly linked to the acoustic response modes of the ball when struck).

As shown, the system 10 may generally include a computing device 12 in communication with a display 14, a user input device 16, and an audio output device 18. As will be explained in greater detail below, the system 10 may be configured to play a plurality of audio files to the user via the audio output device 18, with each audio file corresponding to the acoustic response of a different golf ball model to a standardized impact force. Using the input device 16, the user may select an acoustic response that is most preferred, which the system 10 may then use to suggest an optimal ball.

The display 14, user input device 16 and audio output device 18 may be conventional computer peripherals that can communicate with the computing device 12 via wired or wireless means. For example, the display 14 may be a standard computer monitor that incorporates either liquid crystal display (LCD) technology, or light emitting diode (LED) display technology to generate a visual image. The user input device 16 may allow the user to interact with the computing device 12, and may include one or more of a mouse, a joystick, a keyboard, a push button, or another such input device that is capable of evidencing a user intent. In one configuration, the user input device may be integrated into the display 14 via a digitizer that may respond to physical contact from the user.

The audio output device 18 may include, for example, standard speakers that may convert a received electrical actuation signal into an audible sound wave 20. In another configuration, the audio output device 18 may include studio-quality headphones that are configured to isolate and/or attenuate sounds from the external environment, while providing a high fidelity sound wave 20 to the user. In one configuration, the audio output device 18 may have a +/−3 dB frequency response of from about 80 Hz to about 8 kHz. In another configuration, the +/−3 dB frequency response may more broadly be from about 50 Hz to about 15 kHz. More generally, the audio output device 18 should be selected to at least reproduce the sound of a golf ball impact with reasonable clarity.

The computing device 12 may include a processor 22 and an associated memory 24. The processor 22 may be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EE-PROM), high-speed clock, analog-to-digital (A/D) circuitry, digital-to-analog (D/A) circuitry, input/output (I/O) circuitry, and/or signal conditioning and buffering electronics. The memory 24 may generally be a non-transitory computer readable medium that may store a plurality of digital files 26 readable by the processor 22.

The computing device 12 may be in communication with the display 14, the user input device 16, and the audio output device 18 either locally, or through a network interface. For example, in one configuration, the system 10 may be included in a retail kiosk or interactive ball-fitting system that may be used locally by a consumer to make an educated purchase (e.g., in a retail environment). In another configuration, the system 10 may be an online tool that a consumer may access through a standard web interface.

Figure 2:
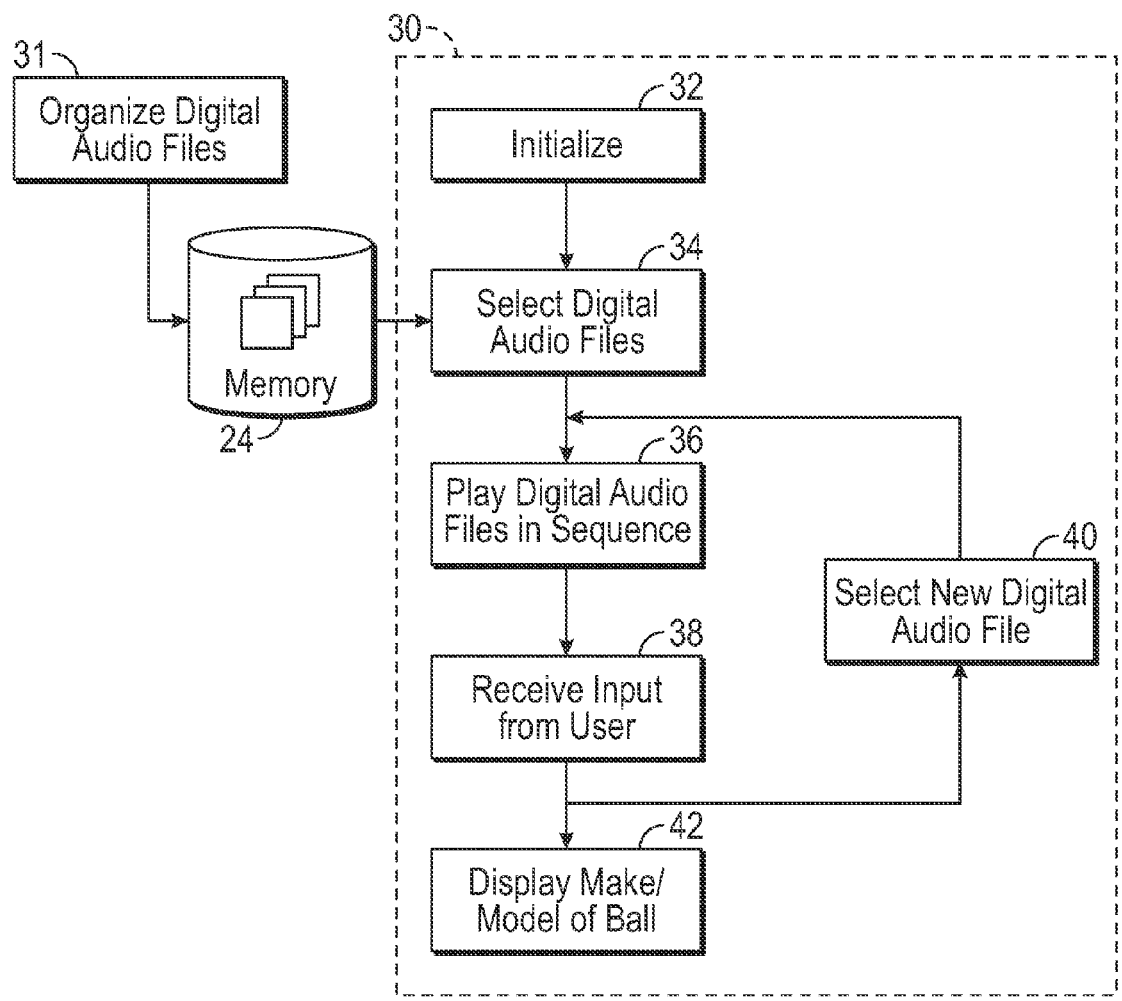
FIG. 2 is a schematic flow chart of a method of matching a user with an optimal golf ball model according to that user's preferences.

FIG. 2 schematically illustrates one embodiment of method 30 that may be used to match a user with an optimal golf ball model according to that user's preferences. The method 30 may be embodied as an algorithm, which may be performed by the processor 22 and/or computing device 12 in combination with the memory 24, display 14, user input device 16, and audio output device 18.

Prior to the performance of the method 30, a plurality of digital audio files 26 may be recorded (at 31) and stored on the memory 24, with each digital audio file 28 corresponding to the acoustic response of a golf ball to a standardized impact force. As used herein, a standardized impact force is a force that is dynamically imparted to a golf ball through a repeatable and consistent process. Examples of different standardized impact forces include, for example, dropping a ball from a predefined height onto a solid surface, and/or striking the ball with a club that is swung in a controlled manner along an arcuate path (e.g., by a testing robot).

Figure 3:
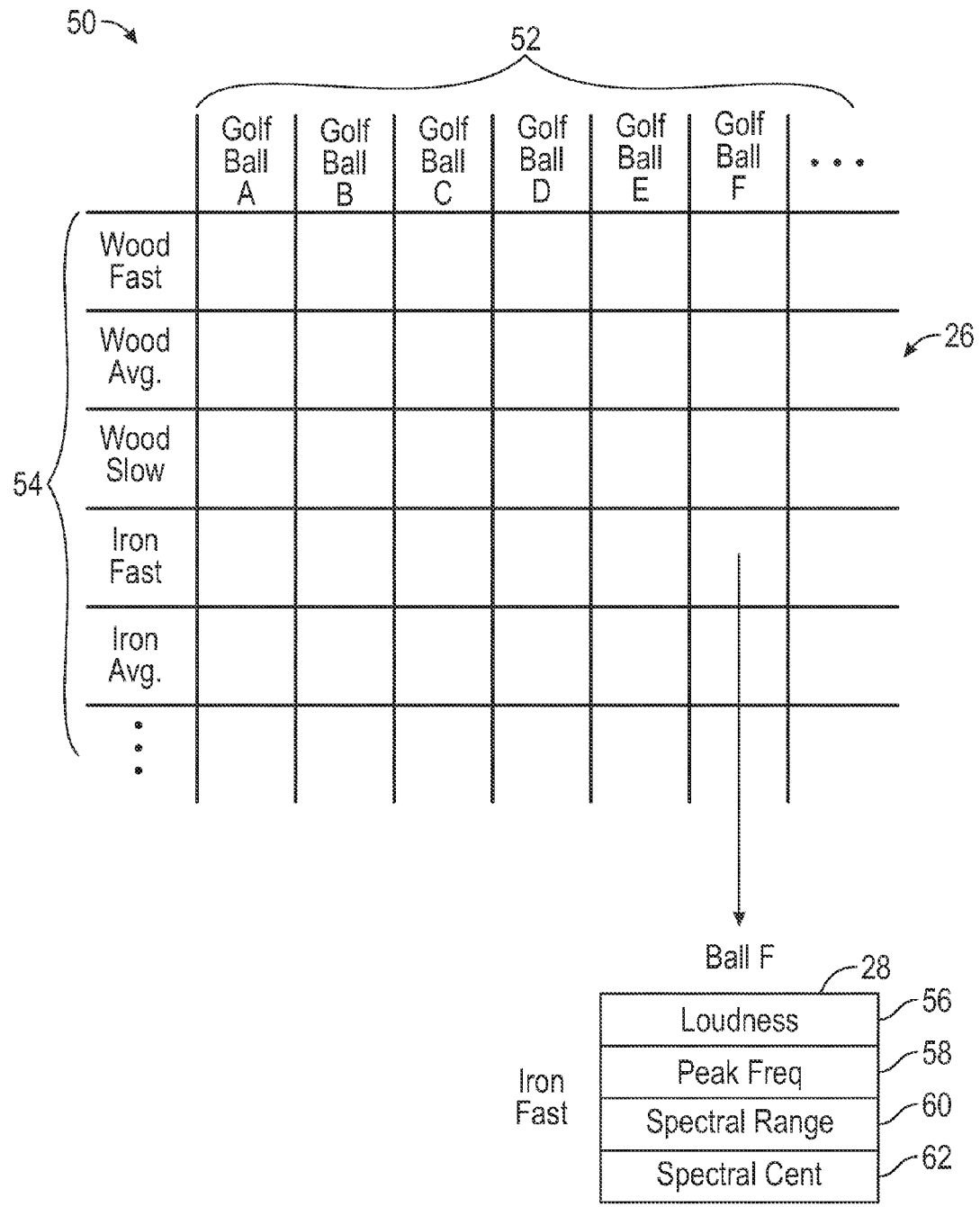
FIG. 3 is a schematic chart illustrating a plurality of digital audio files organized according to a golf ball model type and an impact type.

As schematically shown in the chart 50 provided in FIG. 3, the plurality of digital audio files 26 may correspond to a plurality of different golf ball models 52, each receiving, for example, a plurality of different standardized impact forces 54. Each file 28 may be indexed according to one or more acoustic properties of the resultant impact, such as for example, the loudness of the impact 56, the peak frequency or frequencies of the impact 58, and/or the spectral range 60 or centroid 62 of the impact.

The plurality of golf ball models 52 may include different golf ball models that may be formed from different construction methods or materials, and/or each having different compression ratios. Additionally, the plurality of standardized impact forces 54 may include forces imparted by different club types (e.g., a wood, an iron, a wedge, a putter), and/or forces imparted when the ball is dropped from a fixed distance onto a solid surface. For impact forces that are imparted by a club, these forces may be further characterized by different swing speeds (e.g., slow, average, and fast).

Referring again to FIG. 2, the method 30 of matching a user with an optimal golf ball may generally begin when the user initializes the software via the user interface 16 at step 32. Once initialized, the processor 22 then selects two digital audio files 28 from the associated memory 24 at step 34 (i.e., a first digital audio file, and a second digital audio file), and plays these files in sequence to the user via the audio output device 18 at step 36.

Upon hearing the two golf ball impacts (via the playback of each respective audio file 28), the user may choose the acoustic response that is more desirable or pleasing based on pre-established individual preferences at 38. This choice may be received by the processor 22 via the user input device 16. Once this choice is received, the processor 22 may then either select a new audio file for playback (at 40) using the knowledge of the prior preferred sound, or it may display a model identifier for a ball that corresponds to the identified user preferences and/or preferred acoustic response at 42. In one configuration, the selection of a new audio file for playback at 40 may occur several times until the system has fully identified an optimal acoustic response.

While the above-referenced method 30 illustrates the general ball-matching routine, in further embodiments, additional complexity may be integrated into one or more of the steps, as will be discussed below.

In one configuration, the initialization step 32 may be as simple as pressing a "start" button via the user interface 16. In another configuration, the initialization step 32 may attempt to acquire certain information about the user that may be helpful in selecting an optimal golf ball or narrowing the collection of digital audio files. For example, the system 10 may receive a number of inputs that relate to the ability level and/or preferences of the user. These inputs may then be used to weight or filter the total collection of digital audio files prior to selecting files for playback to provide acoustic responses for only balls that match or maximize other preference or ability criteria.

Figure 4:
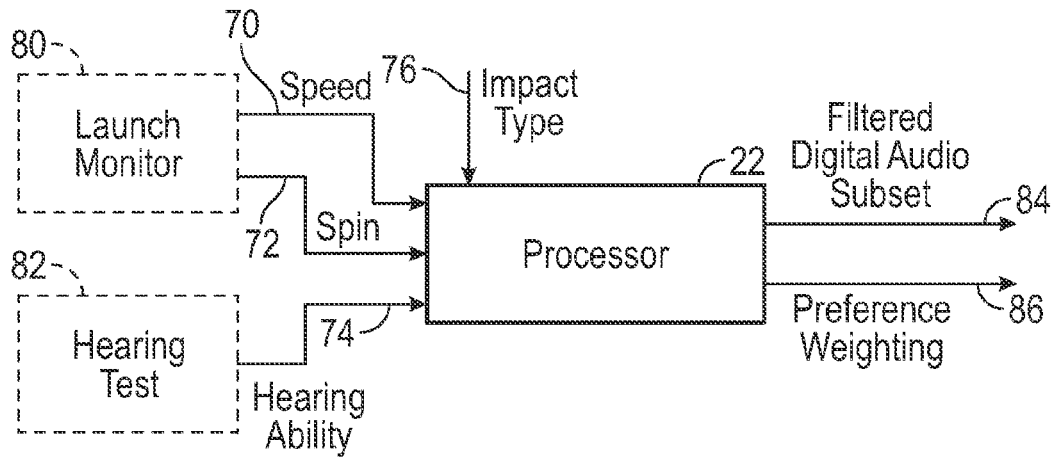
FIG. 4 is a schematic diagram of a system processor accounting for a user's preferences and ability level.

FIG. 4 schematically illustrates an embodiment where four "preference inputs" are received by the system 10 during the initialization step 32. These inputs include the user's typical swing speed 70, spin tendency 72, hearing ability or audible sensitivity 74, and/or the type of impact 76 to be used for the test. In one configuration, each input may either be manually entered via the user interface 16, or may be automatically recorded through the use of one or more automated testing systems. For example, in one configuration the user may enter his typical club head speed 70 and/or spin tendency 72 via the user interface 16. In another configuration the processor 22 may receive these inputs 70, 72 from a launch monitor 80, that may be capable of monitoring an actual club swing by the user (e.g., at a driving range).

With regard to hearing ability/audible sensitivity 74, it is well-known that a person's audible sensitivity changes with age. As such, if the user is unable to hear a particular frequency range, sounds within this particular frequency range should be discounted when selecting an optimal golf ball. In one configuration, the user's audible sensitivity may be statistically determined by asking one or more questions via the display 14 (e.g., the user's age). The answers to these questions may be used to statistically determine a likely range of audible frequencies for that user. In another configuration, the system 10 may conduct a hearing test 82 by playing a series of tonal frequencies to the user via the audio output device 18 and then inquiring if the frequencies were perceivable.

Finally, the system 10 may inquire whether the user is interested in the acoustic response of, for example, a ball being struck by a wood, an iron, a wedge, a putter, or merely the sound of a ball being dropped onto a solid surface.

Once the system has a proper understanding of the user's ability level and audible sensitivity, the processor 22 may filter the entire collection of digital audio files 26 to remove any files that correspond to golf balls not properly suited for the golfer. For example, some golf balls may promote spin over distance. Such a ball may not be properly suited to a high-handicap golfer that favors distance over spin; thus it may be removed from the set of potential matches. Similarly, if two balls are only acoustically different in a range of about 4-5 kHz, and these frequencies are inaudible by the user, other factors such as distance or spin may be more heavily weighted, while the acoustic response is discounted. In this manner, following initialization 32, the processor may establish either a filtered collection of digital audio files 84 to use for subsequent audio testing, or may adjust weighting factors 86 to alter the relative influence of the different user parameters.

Figure 5:
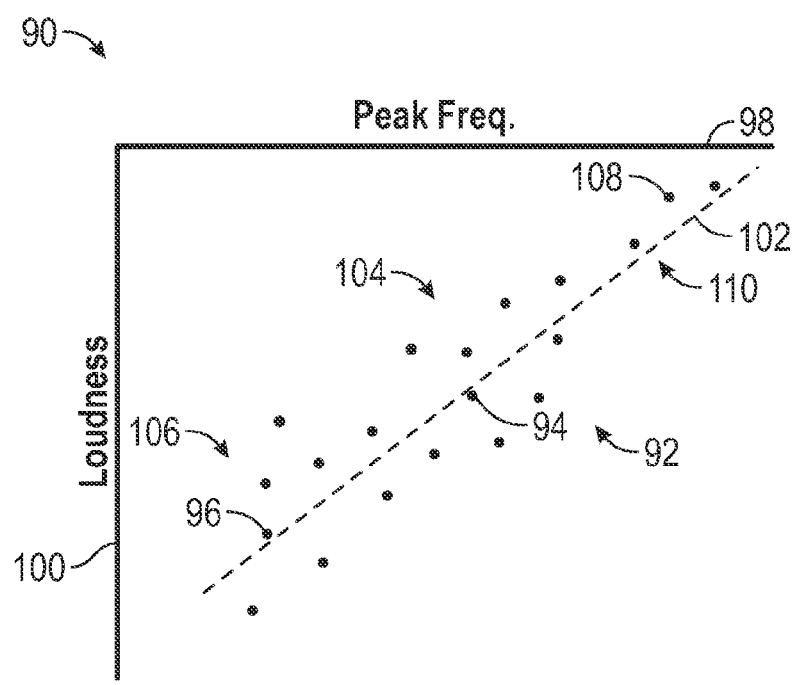
FIG. 5 is a schematic graph of a plurality of acoustic responses indexed according to peak frequency and loudness of the respective acoustic response to a standardized impact force.

Following initialization 32, the processor 22 may then select two digital audio files for playback to the user. In one configuration, the files may be selected to have dissimilar audio characteristics. FIG. 5 schematically illustrates a graph 90 of a plurality of acoustic responses 92 from which the two digital audio files 94, 96 may be selected. While this graph 90 plots peak frequency 98 against the loudness of the response 100, it should be understood that more or fewer factors may be similarly used to select the digital audio files 94, 96. In the embodiment shown, the plotted acoustic responses 92 define a primary trendline 102 that generally has a positive slope. The initial two audio files 94, 96 may be selected, for example, such that the first file 94 represents an acoustic response in a central portion 104 of the trendline 102, and the second file 96 represents an acoustic response at an extreme 106 of the trendline 102.

Once selected (at step 34), the two files 94, 96 may then be played for the user (at step 36), and the user may select their preferential sound via the user interface 16 (at step 38). If, for example, the first file 94 is found to be more preferential (i.e., from the central portion 104 of the trendline 102), the processor 22 may then select a third digital audio file 108 (at step 40) for example from the opposite extreme 110 of the trendline 102. The first and third audio files 94, 108 may then be played (at step 36) for the user to further refine the system's understanding of the user's preference.

While this central/extreme selection method is one example of a manner to select the digital audio files to most rapidly arrive at a preferred sound, it should be appreciated that other manners of selecting the files may similarly be used. For example, in another configuration, the system 10 made divide the files into quadrants according to indexed acoustic parameters, and select files from each quadrant. Likewise, instead of a binary selection between two sounds, alternatively, the system 10 may ask the user to rank the sound on a sliding scale, and may use the subjective scoring to arrive at an optimal response.

Once the system 10 determines the preferred acoustic response, it may then present the user with a model identifier for the ball that corresponds to the user's preferences (at step 42). In one configuration, the model identifier may be selected, for example, by directly referencing the preferred acoustic response and the model of the ball that corresponds to that response. In another configuration, a weighting algorithm may be used (e.g., according to the weighting factors 80 established during the initialization step 32) to determine an optimal golf ball according to the user's preference for distance, spin, sound, or other factors. For example, if a user is unable to hear a particular acoustic response, the algorithm may more heavily weight factors such as distance or spin. Similarly, if it is established that the users primary concern is the acoustic response of the ball, then distance and/or speed may be less heavily weighted than the acoustic properties.

As mentioned above, the acoustic response of a ball to an impact force has been found to be a primary contributor to the perceived "feel" of the ball by a golfer. Therefore, while it is possible to merely playback the digital audio files via a speaker associated with a retail kiosk, ball fitting system, or internet browser, in another configuration the sounds may be simulated during the process of an actual swing. In this configuration, the user may wear headphones that are capable of isolating and/or attenuating external sounds. The playback of the digital audio file (at step 36) may then be timed appropriately to correspond with the moment of actual impact by the user against a ball (e.g., sensed by a launch monitor, optical recognition system, radar, pressure sensor disposed on a club, etc, such as at a driving range or practice facility). In doing so, rather than merely choosing between audio responses, the audio would then be more appropriately perceived as the "feel" of the ball.

While the best modes for carrying out the invention have been described in detail, those familiar with the art to which this invention relates will recognize various alternative designs and embodiments for practicing the invention within the scope of the appended claims. It is intended that all matter contained in the above description or shown in the accompanying drawings shall be interpreted as illustrative only and not as limiting.

What is claimed is:

1. An electronic method for matching a user with a golf ball, the method comprising:
    playing a first digital audio file to a user via a computer, the first digital audio file corresponding to an acoustic response of a first golf ball to a standardized impact force;
    playing a second digital audio file to the user via the computer, the second digital audio file corresponding to an acoustic response of a second golf ball to the standardized impact force;
    receiving an input from the user via the computer, the input corresponding to a preferred acoustic response selected from the acoustic response of the first golf ball and the acoustic response of the second golf ball; and
    displaying a golf ball model that corresponds to the preferred acoustic response.

2. The method of claim 1, further comprising storing on the computer a plurality of digital audio files, including the first digital audio file and the second digital audio file, wherein each file of the plurality of digital audio files corresponds to the acoustic response of a different golf ball model to the standardized impact force.

3. The method of claim 2, further comprising indexing the plurality of digital audio files on a range according to the magnitude of an acoustic property selected from a loudness, a peak frequency, and a spectral centroid.

4. The method of claim 3, selecting each of the respective first digital audio file and the second digital audio file from the plurality of digital audio files in an iterative manner according to a user preference for the acoustic property.

5. The method of claim 2, further comprising receiving a preference input from the user corresponding to at least one of a distance preference, a spin tendency, and an audible sensitivity of the user;

filtering the plurality of digital audio files using the received preference input to form a filtered collection of digital audio files; and wherein the first digital audio file and the second digital audio file are selected from the filtered collection of digital audio files.

6. The method of claim 1, wherein the standardized impact force is an impact force generated by dropping the respective golf ball from a predetermined height onto a solid material.

7. The method of claim 1, wherein the standardized impact force is an impact force imparted to the respective golf ball by a golf club head swung at a controlled speed and angle.

8. The method of claim 7, further comprising receiving a second input from the user, via the computer, the second input corresponding to a type of the golf club used to impart the impact force to the golf ball.

9. The method of claim 8, wherein the type of golf club is selected from a wood, an iron, a wedge, and a putter.

10. A method for matching a user with a golf ball, the method comprising:
    providing a computer having stored therein a plurality of digital audio files, each digital audio file corresponding to an acoustic response of a respective golf ball to a standardized impact force;
    playing a first digital audio file to the user via an audio playback device, the first digital audio file selected from the plurality of digital audio files, and corresponding to a first acoustic response;
    playing a second digital audio file to the user via the audio playback device, the second digital audio file selected from the plurality of digital audio files, and corresponding to a second acoustic response;
    receiving a first input from the user via the computer, the first input corresponding to a first preferred acoustic response selected from the first acoustic response and the second acoustic response;
    playing a third digital audio file to the user via the audio playback device, the third digital audio file selected from the plurality of digital audio files, and corresponding to a third acoustic response;
    receiving a second input from the user via the computer, the second input corresponding to a second preferred acoustic response selected from the first preferred acoustic response and the third acoustic response;
    displaying a golf ball model that corresponds to the second preferred acoustic response.

11. The method of claim 10, wherein the standardized impact force is an impact force generated by dropping the respective golf ball from a predetermined height onto a solid material.

12. The method of claim 10, wherein the standardized impact force is an impact force imparted to the respective golf ball by a golf club head swung at a controlled speed and angle.

13. The method of claim 12, further comprising receiving a second input from the user, via the computer, the second input corresponding to a type of the golf club used to impart the impact force to the golf ball.

14. The method of claim 13, wherein the type of golf club is selected from a wood, an iron, a wedge, and a putter.

15. The method of claim 10, further comprising receiving a preference input from the user corresponding to at least one of a distance preference, a spin tendency, and an audible sensitivity of the user;
    filtering the plurality of digital audio files using the received preference input to form a filtered collection of digital audio files; and
    wherein the first digital audio file, the second digital audio file, and the third digital audio file are selected from the filtered collection of digital audio files.

* * * * *